United States Patent
Bornzin

(10) Patent No.: US 7,756,570 B1
(45) Date of Patent: Jul. 13, 2010

(54) METHODS AND ARRANGEMENTS FOR REDUCING OVERSENSING AND/OR PROVIDING DIAGNOSTIC INFORMATION IN IMPLANTABLE MEDICAL DEVICES

(75) Inventor: Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 475 days.

(21) Appl. No.: 11/414,837

(22) Filed: May 1, 2006

(51) Int. Cl.
*A61N 1/05* (2006.01)
(52) U.S. Cl. .............................. 600/509; 607/5; 607/7; 600/508; 600/515; 600/516; 600/517; 600/518; 600/521; 128/898; 128/899; 128/920
(58) Field of Classification Search ......... 600/508–509, 600/515–518, 521; 607/5, 7; 128/898–899, 128/920
See application file for complete search history.

(56) References Cited

U.S. PATENT DOCUMENTS

| | | | |
|---|---|---|---|
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | 128/419 PG |
| 4,729,376 A | 3/1988 | DeCote, Jr. | 128/419 PT |
| 4,766,902 A | 8/1988 | Schroeppel | 128/419 PG |
| 4,768,511 A | 9/1988 | DeCote, Jr. | 128/419 PG |
| 4,788,980 A | 12/1988 | Mann et al. | 128/419 PG |
| 4,809,697 A | 3/1989 | Causey, III et al. | 128/419 PT |
| 4,940,052 A | 7/1990 | Mann et al. | 128/419 PG |
| 4,940,054 A * | 7/1990 | Grevis et al. | 607/4 |
| 4,944,298 A | 7/1990 | Sholder | 128/419 PG |
| 4,944,299 A | 7/1990 | Silvian | 128/419 PG |
| 4,960,123 A | 10/1990 | Maker | 128/419 D |
| 4,969,467 A | 11/1990 | Callaghan et al. | 128/419 PG |
| 5,350,410 A | 9/1994 | Kleks et al. | 607/28 |
| 5,374,282 A | 12/1994 | Nichols et al. | 607/18 |
| 5,466,254 A | 11/1995 | Helland | 607/123 |
| 5,476,483 A | 12/1995 | Bornzin et al. | 607/17 |
| 5,564,430 A | 10/1996 | Jacobson et al. | 128/697 |
| 5,573,550 A | 11/1996 | Zadeh et al. | 607/28 |
| 5,685,315 A | 11/1997 | McClure et al. | 128/708 |
| 5,718,242 A * | 2/1998 | McClure et al. | 600/515 |
| 5,778,881 A * | 7/1998 | Sun et al. | 600/509 |
| 5,891,171 A | 4/1999 | Wickham | 607/4 |
| 6,169,918 B1 | 1/2001 | Haefner et al. | |
| 6,192,273 B1 | 2/2001 | Igel et al. | |

(Continued)

FOREIGN PATENT DOCUMENTS

EP 0 334 618 B1 1/1995

OTHER PUBLICATIONS

NonFinal Office Action, mailed Aug. 23, 2005: Related U.S. Appl. No. 10/310,485.

(Continued)

*Primary Examiner*—Carl H Layno
*Assistant Examiner*—Deborah Malamud

(57) ABSTRACT

An exemplary method to reduce risk of ventricular oversensing includes sensing, in vivo, amplitude of electrical cardiac activity, comparing sensed amplitude to a low sensitivity threshold where if the comparing indicates that sensed amplitude does not meet or exceed the low sensitivity threshold then further comparing the sensed amplitude to a high sensitivity threshold and if the further comparing indicates that sensed amplitude meets or exceeds the high sensitivity threshold then determining that ventricular fibrillation may exist. Various exemplary devices, systems, methods, etc., are disclosed.

9 Claims, 9 Drawing Sheets

U.S. PATENT DOCUMENTS

| | | |
|---|---|---|
| 6,275,734 B1 | 8/2001 | McClure et al. ................ 607/27 |
| 6,434,426 B1 | 8/2002 | Munneke et al. ............... 607/27 |
| 6,480,739 B1 | 11/2002 | Nigam et al. |
| 6,584,350 B2 * | 6/2003 | Kim et al. ....................... 607/5 |
| 6,772,009 B2 | 8/2004 | Zhang et al. .................... 607/9 |
| 2002/0165587 A1 | 11/2002 | Zhang et al. ................... 607/28 |

OTHER PUBLICATIONS

NonFinal Office Action, mailed Nov. 5, 2005: Related U.S. Appl. No. 10/310,485.

Final Office Action, mailed May 9, 2006: Related U.S. Appl. No. 10/310,485.

Advisory Action, mailed Jul. 26, 2006: Related U.S. Appl. No. 10/310,485.

NonFinal Office Action, mailed Aug. 24, 2006: Related U.S. Appl. No. 10/310,485.

Final Office Action, mailed Feb. 1, 2007: Related U.S. Appl. No. 10/310,485.

Advisory Action, mailed Apr. 23, 2007: Related U.S. Appl. No. 10/310,485.

NonFinal Office Action, mailed Jul. 2, 2007: Related U.S. Appl. No. 10/310,485.

* cited by examiner

METHODS AND ARRANGEMENTS FOR REDUCING OVERSENSING AND/OR PROVIDING DIAGNOSTIC INFORMATION IN IMPLANTABLE MEDICAL DEVICES

RELATED APPLICATIONS

This application is related to co-pending U.S. patent application Ser. No. 10/310,485, filed Dec. 4, 2002, which is incorporated by reference herein.

FIELD OF THE INVENTION

Subject matter presented herein generally relates to implantable medical devices and more particularly concerns improved methods and arrangements for reducing oversensing and/or providing diagnostic information in implantable medical devices.

BACKGROUND OF THE INVENTION

The major pumping chambers in the human heart are the left and right ventricles. The simultaneous physical contraction of the myocardial tissue in these chambers expels blood into the aorta and the pulmonary artery. Blood enters the ventricles from smaller antechambers called the left and right atria, which contract about 100 milliseconds (ms) before the ventricles. This interval is known as the atrioventricular (AV) delay. The physical contractions of the muscle tissue result from the depolarization of such tissue, which depolarization is induced by a wave of spontaneous electrical excitation which begins in the right atrium, spreads to the left atrium and then enters the AV node which delays its passage to the ventricles via the so-called bundle of His. The frequency of the waves of excitation is normally regulated metabolically by the sinus node. The atrial rate is thus referred to as the sinus rate or sinus rhythm of the heart.

Electrical signals corresponding to the depolarization of the myocardial muscle tissue appear in the patient's electrocardiogram. A brief, low-amplitude signal known as the P-wave accompanies atrial depolarization normally followed by a much larger amplitude signal, known as the QRS complex, with a predominant R-wave signifying ventricular depolarization. Repolarization prior to the next contraction is marked by a broad waveform in the electrocardiogram known as the T-wave.

A typical implanted cardiac pacer (or pacemaker) operates by supplying missing stimulation pulses through an electrode on a pacing lead in contact with the atrial or ventricular muscle tissue. The electrical stimulus independently initiates depolarization of the myocardial (atrial or ventricular) tissue resulting in the desired contraction. The P-wave or R-wave can be sensed through the same lead (i.e., the pacing lead) and used as a timing signal to synchronize or inhibit stimulation pulses in relation to spontaneous (natural or intrinsic) cardiac activity. The sensed P-wave or R-wave signals are referred to as an atrial electrogram or ventricular electrogram, respectively.

Modern-day implantable stimulation devices include cardiac event detecting/sensing circuitry, whether the activity of one or both chambers of the heart are sensed. A cardiac event is essentially detected when the sensed electrogram signal exceeds a defined sensitivity threshold level. If the sensitivity level is too low (e.g., the sensitivity threshold is set too high), then some intrinsic cardiac events may not be detected. If the sensitivity level is too high (e.g., the sensitivity threshold is set too low) then, on the other hand, the high gain of the amplifier may cause noise or T-wave signals to be sensed, giving rise to erroneous classifying of noise as a cardiac event. Devices provided with communications telemetry (e.g., noninvasive programming capabilities) advantageously allow the physician to manually set the sensitivity level.

There are at least two disadvantages to having the physician set the sensitivity level. First, adjusting the sensitivity level is one more thing that the physician must remember to do, and it would be advantageous to relieve him or her of that task if it is possible to do so. Secondly, and more important, the physician generally sees the patient only occasionally, and weeks or months may go by without the sensitivity level being changed. Problematically, the sensitivity level that will accurately detect cardiac events at a given threshold level for a patient does not stay static; e.g., the R-wave amplitude and frequency content can vary considerably within a given patient. Thus, changes in the sensitivity level are needed to accommodate for physical and mental stress. In addition, the sensitivity level needs to change as myocardial tissue (heart muscle tissue) undergoes scarring or other physical responses to the implanted electrogram lead(s). Furthermore, other changes in the myocardium-electrogram lead interface, e.g., shifting of the position of the electrogram lead, may also cause changes in the proper sensitivity level. There may also be a need to change the sensitivity due to internal and/or external electrical noise.

Unfortunately, many of these changes occur over a period of days and, in some cases, even hours or minutes. Because the physician generally sees the patient only every few weeks or months, the pacemaker sensing circuits can erroneously detect, or not detect, cardiac events over large periods of time. This erroneous detection/non-detection can cause under-pacing or over-pacing of the heart. Unfortunately for the patient, such changes may potentially leave him or her in a worse condition than he or she was in before the stimulation device was implanted. At best, the stimulation device is not able to operate efficiently—for example, by either unnecessarily providing therapy and thereby draining the battery and risking pacemaker-induced tachycardias; and/or not providing therapy as often as is needed by the patient.

Consequently, there is a need for improved methods and arrangements for dynamically adjusting the sensitivity of an implantable device to account for potential changes in the electrogram signal. Further, a need exists, as explained further below, for methods, devices, etc., that act to reduce risk of oversensing in implantable cardiac defibrillation devices (ICDs). Various exemplary methods, devices, systems, etc., presented herein aim to address these needs and/or other needs.

SUMMARY

An exemplary method to reduce risk of ventricular oversensing includes sensing, in vivo, amplitude of electrical cardiac activity, comparing sensed amplitude to a low sensitivity threshold where if the comparing indicates that sensed amplitude does not meet or exceed the low sensitivity threshold then further comparing the sensed amplitude to a high sensitivity threshold and if the further comparing indicates that sensed amplitude meets or exceeds the high sensitivity threshold then determining that ventricular fibrillation may exist. Such an exemplary may include determining whether to call for charging a charge storage and/or delivery of a defibrillation shock, based at least in part on the comparing to a low sensitivity, the comparing to a high sensitivity or the comparing to a low sensitivity and the comparing to a high sensitivity.

An exemplary implantable device includes means for sensing amplitude of electrical cardiac activity, means for comparing sensed amplitude to at least a low sensitivity threshold and a high sensitivity threshold and means for determining whether to charge a charge storage of the implantable device based at least in part on the comparing. Such an exemplary device optionally includes logic to decide whether to call for delivery of a defibrillation shock. Other exemplary devices, systems, methods, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENT

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Methods and arrangements are provided herein which automatically adjust the sensitivity of an implantable stimulation device upon detection of high amplitude noise in a sensed electrogram during a refractory period following the detection of a sensed event in a heart. In accordance with certain implementations of the present invention, for example, if the amplitude of the electrogram signal exceeds an initial sensitivity threshold amplitude value during a ventricular refractory period following the detection of an R wave, then the sensitivity threshold amplitude value is selectively temporarily increased at least once, thereby decreasing the sensitivity for a defined period of time. The resulting decreased sensitivity tends to significantly prevent any subsequent similarly high amplitude noise from being over sensed once the refractory period has ended. The switching from a high sensitivity level to a lower sensitivity level preferably occurs during the refractory period to prevent artificial noise caused by the switching process from causing a false positive detection. Similarly, the switching back from the lower sensitivity level to the higher sensitivity level preferably occurs during a subsequent blanking period to prevent a false positive detection.

Exemplary Stimulation Device

The techniques described below are intended to be implemented in connection with any stimulation device that is configured or configurable to stimulate or shock a patient's heart.

Figure 1:
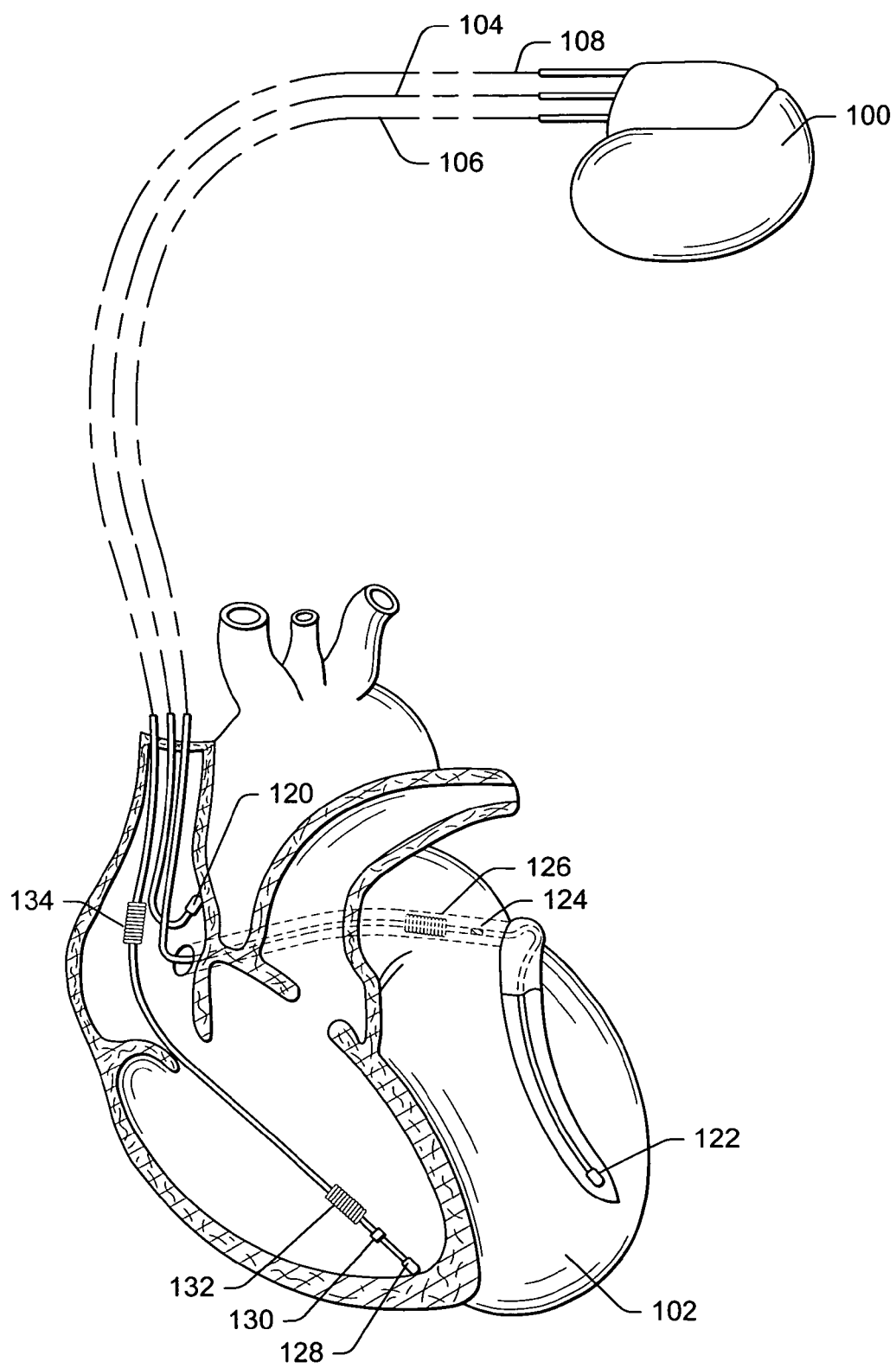
FIG. 1 is a simplified diagram illustrating an implantable stimulation device in electrical communication with at least three leads implanted into a patient's heart for delivering multi-chamber stimulation and shock therapy, in accordance with certain exemplary implementations of the present invention.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
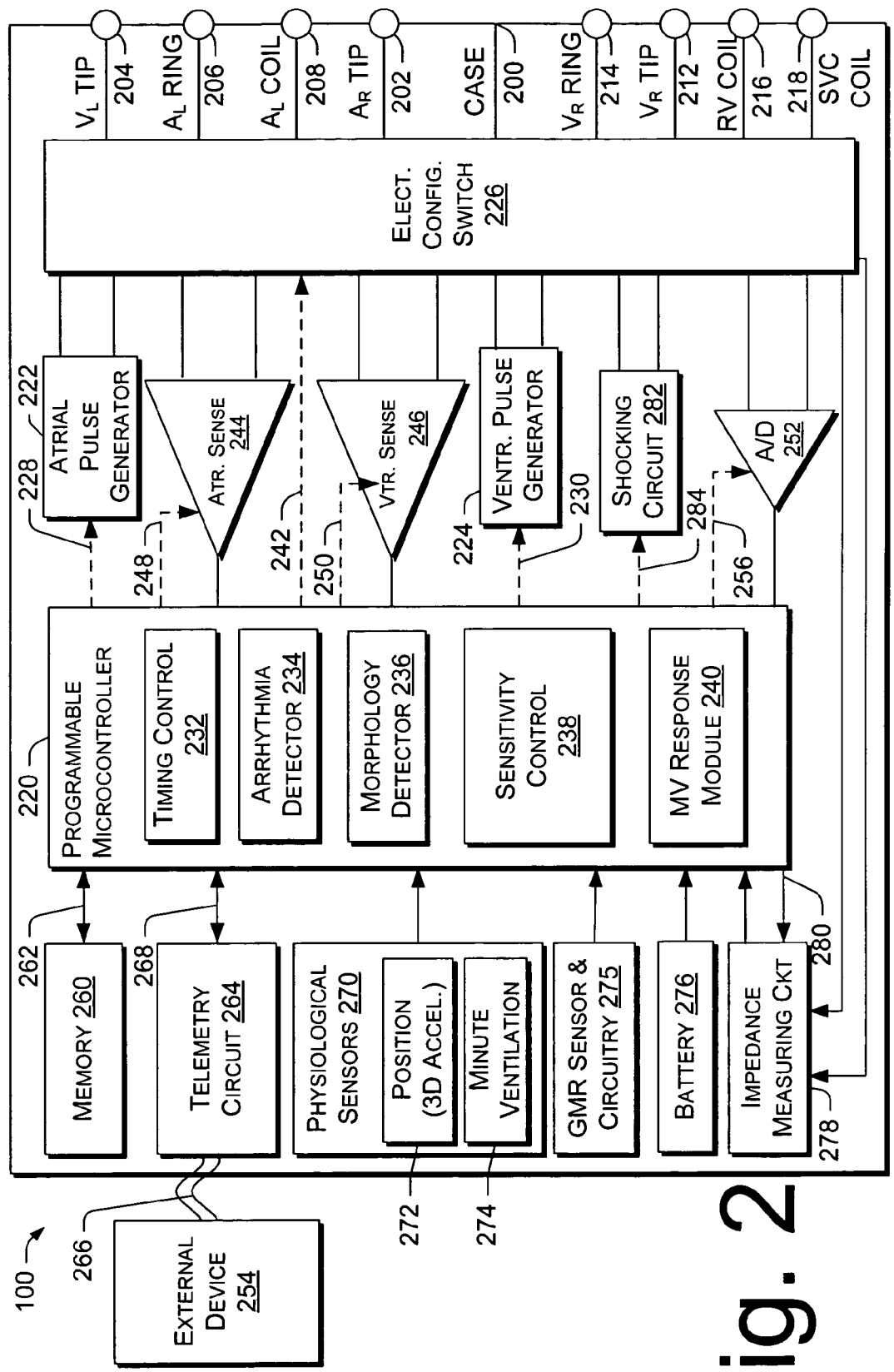
FIG. 2 is a functional block diagram of a multi-chamber implantable stimulation device illustrating basic elements that are configurable to monitor cardiac signals and provide stimulation pulse waveforms to a heart, as needed, in accordance with certain exemplary implementations of the present invention.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry/logic in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular ring electrode 122, the left atrial tip electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, a sensitivity control 238, and a minute ventilation (MV) response module 240. These components can be utilized by the stimulation device 100 for determining desirable times to administer various therapies. The components 234-240 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. In certain implementations, a plurality of sensing circuits may be provided. Switch 226 determines the "sensing polarity" of the cardiac signal by selectively closing the appropriate switches, as is also known in the art. In this way, the clinician may program the sensing polarity independent of the stimulation polarity.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. In accordance with certain implementations of the present invention, sensitivity control 238 is configured to selectively program or otherwise change the gain and/or a threshold value to either increase or decrease the sensitivity of ventricular sensing circuit 246.

Those skilled in the art will recognize that the methods and arrangements provided herein are also clearly adaptable to atrial sensing and therapy.

The automatic gain control enables the device 100 to deal effectively with the difficult problem of sensing the low amplitude signal characteristics of atrial or ventricular fibrillation. For a complete description of a typical sensing circuit, the reader is directed to U.S. Pat. No. 5,573,550, entitled "Implantable Stimulation Device having a Low Noise, Low Power, Precision Amplifier for Amplifying Cardiac Signals" (Zadeh et al.). For a complete description of an automatic gain control system, the reader is directed to U.S. Pat. No. 5,685,315, entitled "Cardiac Arrhythmia Detection System for an Implantable Stimulation Device" (McClure et al.). Accordingly, the '550 and the '315 patents are hereby incorporated herein by reference.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. As used herein "sensing" is reserved for the noting of an electrical signal, and "detection" is the processing of these sensed signals, and noting the presence of an arrhythmia, for example. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

Advantageously, the data acquisition system 252 may be coupled to the microcontroller 220, or other detection circuitry, for detecting an evoked response from the heart 102 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See, for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), all of which are hereby incorporated herein by reference. The type of capture detection system used is not critical to the described implementations.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are incorporated herein by reference.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which patent is hereby incorporated by reference.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 preferably employs lithium/silver vanadium oxide batteries, as is true for most (if not all) current devices.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to about 0.5 joules), moderate (e.g., about 0.5 to about 10 joules), or high energy (e.g., about 11 to about 40 joules), as controlled by the microcontroller 220.

Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (e.g., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of about 5 to about 40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

The operation of sensitivity control 238, within programmable microcontroller 220 will now be described in greater detail according to certain implementations of the present invention. The module 238 may perform any of a variety of actions or implement control logic related to acquiring information (e.g., sensing, etc.) comparisons of cardiac electrical activity to sensitivity thresholds or morphologies and calls for action based at least in part on such comparisons.

Figure 3:
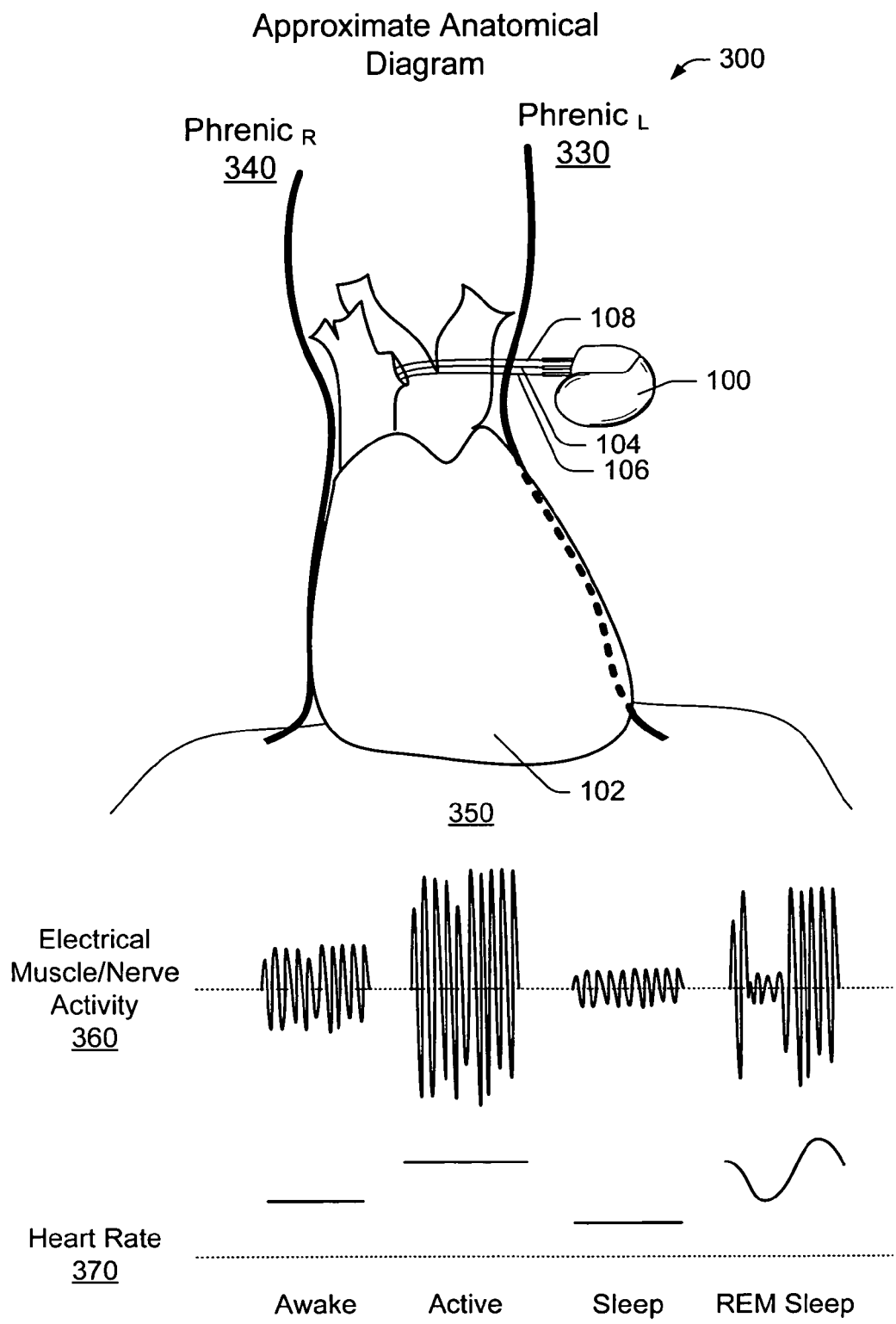
FIG. 3 is an approximate anatomical diagram of the heart, phrenic nerves and the diaphragm that includes plots of electrical activity and associated heart rate.

FIG. 3 shows an approximate anatomical diagram 300 that includes an implanted stimulation device 100. The implanted stimulation device 100 includes various leads 104, 106, 108, for example, as described with respect to FIG. 1 and FIG. 2. As shown, the left phrenic nerve 330 and the right phrenic nerve 340 pass proximate to the heart 102. In general, the phrenic nerves 330, 340 run from above the subclavian veins and down around the heart 102 (e.g., left and right side) to the surface of diaphragm 350. The right phrenic nerve 320 runs along the intimal tissue of the superior vena cava and the left phrenic nerve 330 runs near the innominate vein. The phrenic nerves 330, 340 innervate the diaphragm 350, which is responsible at least in part for respiration, noting that all branches and fibers of the various nerves are not shown. The diaphragm 350 is segmented into approximately two hemidiaphragms; thus, the right phrenic nerve 340 may act to activate primarily the right hemidiaphragm while the left phrenic nerve 330 may act to activate primarily the left hemidiaphragm.

The lead 106 of the implanted stimulation device 100 may pass transvenously through the right atrium of the heart 102, through the coronary sinus ostium, into the coronary sinus vein and into a surface vein of the heart 102, which is proximate to the left ventricle. In some instances, one of the leads may include an electrode positioned in a vein on an anterior or lateral surface of the heart 102. In this position, the implanted stimulation device 100 may, via a lead and/or an associated electrode, be quite susceptible to electrical noise from the left phrenic nerve 330. Further, the implanted stimulation device 100 may, via leads and/or electrodes positioned on the right side of the heart 102 (e.g., right atrial wall, SVC, IVC, etc.), be quite susceptible to electrical noise form the right phrenic nerve 340. While FIG. 3 shows the diaphragm 350 and phrenic nerves 330, 340, other nerves and/or muscles may produce substantial electrical noise. For example, respiratory muscles such as the genioglossus and nerves such as the hypoglossal can produce electrical noise.

Electrical noise associated with respiration has been termed "respirophasic" noise and know to contribute to oversensing and, in turn, spurious detections and implementation of unwarranted cardiac therapies (e.g., tachyarrhythmia, pacing inhibition, etc.). Electrical noise from other physiological or external sources may also contribute to oversensing. A study by Weretka et al. ("Ventricular oversensing: a study of 101 patients implanted with dual chamber defibrillators and two different lead systems", *Pacing Clin Electrophysiol.*, 2003 January; 26(1 Pt 1):65-70), determined that common pitfalls of ventricular sensing involved T wave oversensing, respirophasic ventricular oversensing, and P wave oversensing, wherein the latter was unique to the tested integrated lead system (in contrast to the tested dedicated bipolar lead system). The study also reported that some patients received inappropriate ICD shocks in response to ventricular oversensing and that patients with cardiomyopathies are more prone to oversensing than patients with other heart diseases.

A plot 360 shows various waveforms representative of electrical noise from muscle and/or nerve activity while a plot 370 shows heart rates that may be associated with the various waveforms. In particular, the waveforms and the heart rates serve to illustrate exemplary behavior during the following patient activity states: Awake, Active, Sleep, and REM Sleep. In general, electrical noise increases with patient activity; therefore, electrical noise may typically be at a minimum during sleep (Sleep) and a maximum during exercise or other strenuous activity (Active). However, during REM sleep, a patient may be sporadically active resulting in variations in muscle/nerve activity and heart rate.

Figure 4:
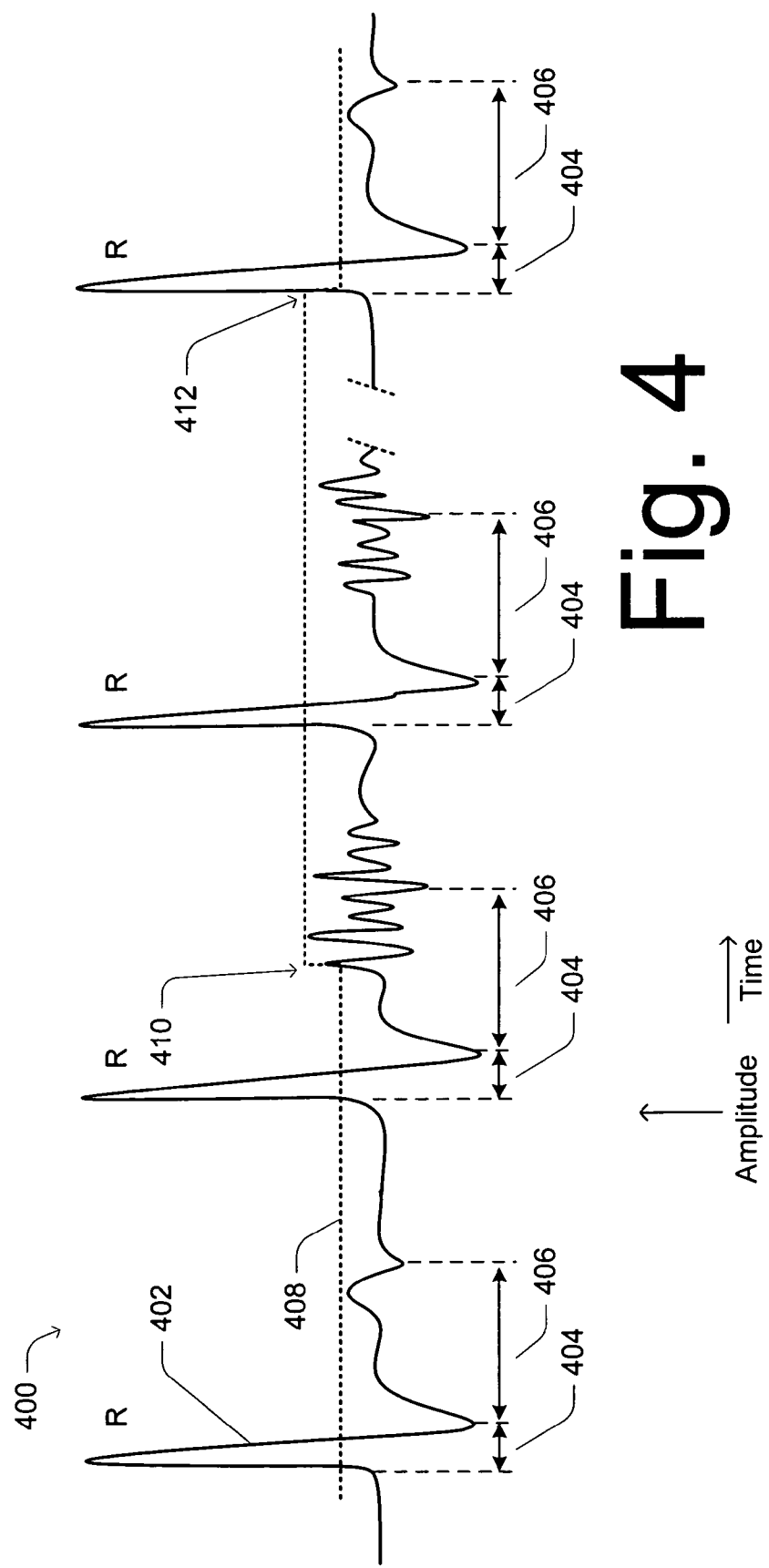
FIG. 4 and FIG. 5 are graphs depicting electrogram signals that include noise and dynamically adjusted threshold values designed to significantly avoid false positive detection of the noise, in accordance with certain exemplary implementations of the present invention.

Attention is drawn to the exemplary timeline graph 400 depicted in FIG. 4. Here, an electrogram 402 (e.g., an intracardiac electrogram) is shown as sensed in the ventricle of a heart. Electrogram 402 includes a plurality of R waves. Associated with the detection of each R wave is a ventricular blanking period 404 and at least one ventricular refractory period 406. Note that timeline graph 400 is broken between two R waves to represent that other R waves, etc., may occur there between.

Also depicted in FIG. 4 is a ventricular threshold amplitude (value) 408, in accordance with certain exemplary implementations of the present invention. Here, the ventricular threshold amplitude 408 is selectively controlled by sensitivity control 238. As shown, ventricular threshold amplitude 408 starts out a first level, i.e., a lower level, which causes the sensing circuit to have a higher sensitivity. In this example, the first R wave in FIG. 4 is detected since it clearly exceeds the lower level threshold value. No other events are detected until the second R wave occurs, because the electrogram never exceeded the lower threshold value until then. Upon detecting the second R wave, there is a blanking period 404 during which no detection occurs. Following the blanking period, there is a refractory period 406, wherein no therapy is applied.

During this refractory period (or periods) the electrogram is depicted as having significant flux, which in this example is noise caused by various sources. At a time 410, during refractory period 406, the "noise" exceeds the lower level threshold value. When this occurs, sensitivity control 238 selectively decreases the sensitivity of the sensing circuitry. Depending upon the implementation, the sensitivity can be decreased in a variety of ways. For example, the gain on a sense amplifier can be decreased. In other implementations, increasing the threshold amplitude or value decreases the sensitivity. For demonstrative purposes, the later sensitivity lowering technique is shown in FIG. 4. Here, at time 410, ventricular threshold amplitude 408 is increased to a higher threshold value, thereby decreasing the sensitivity of the sensing circuitry.

Ventricular threshold amplitude 408 remains at this higher level threshold value for a defined period of time. In graph 400, the higher level threshold value has advantageously prevented false positive detections (of the noise) during the defined period of time, while still allowing the next R wave to be detected.

At time 412, the defined period of time ends, and the ventricular threshold amplitude 408 is switched back to the lower level threshold value. This switching occurs during a blanking period to prevent artificial noise generated by the switch from interfering with the sensing of actual events, and/or noise detection during the subsequent refractory period.

The defined period of time, in accordance with certain implementations of the present invention, can be associated with a clocking signal or the like, based on R wave detections, based on pacing cycles, or the like. By way of example, in certain implementations, the defined period of time has been determined by anywhere from the 1 to about 16 intrinsic/paced cardiac cycles. Of course, the defined period of time may be longer than this. Additionally, other sensed information may be considered in defining the period of time. For example, information about the patient's activity level, etc., may be considered in determining the length of the defined period of time at which the sensitivity remains lower. Hence, in certain implementations, the defined period of time may be dynamically determined. In other implementations, the defined period of time is static, as programmed by the physician or set during manufacture.

At the end of the defined period of time, the lowered threshold value allows the device to check to see if the noise is still present. If noise is still present, then the threshold is again increased for the defined period of time. This can continue indefinitely. This "monitoring" process not only provides improved sensing (reduced false positive detections caused by noise), but also allows for improved detection of premature ventricular contractions (PVCs) and/or other arrhythmias, which may be more easily detected when the stimulation device is operating in a higher sensitivity state.

The actual level of the higher and lower threshold values (or sensitivity levels) may be dynamically determined or predefined (by the physician or during manufacture). For example, in certain implementations, the threshold levels are determined based on the amplitude(s) of one or more detected R waves. Such detection may rely on information from a morphology module (e.g., the module 236) and/or other modules and/or sensors. Thus, the higher threshold (lower sensitivity) may be set to equal about ⅓ or ½ (or some other fraction or percentage) of the amplitude of the R wave(s) (or, e.g., an R wave average, or an R wave measured by a physician, etc.). Here, for example, assuming that the R wave amplitude is about 8 millivolts (mV), then the lower level threshold may be set to about 1-2 mV and the higher level threshold may be set to about 3-4 mV. It is not uncommon for the noise to be 2-3 mV depending on sensing configuration, patient condition, patient, etc., so in some situations these threshold values may each need to be higher or may be lower.

The R wave may also be significantly higher (e.g., about 15 mV or more). Preferably, it would be beneficial to detect PVCs and other arrhythmias, which may have amplitudes of about 2-5 mV or more. Thus, for example, in certain patients, a lower level threshold value of about 2 mV and an upper threshold value of about 4 mV would tend to prevent false positive detections from most noises, while also allowing for detection of PVCs and other arrhythmias.

In other examples described herein, more than one threshold may be used and thresholds may include an upper bound and a lower bound wherein the upper and lower bounds are substantially centered about a baseline or other value. In some instances, a low sensitivity threshold and a high sensitivity threshold are applied to intracardiac electrogram information. Such thresholds may determine if an intracardiac electrogram amplitude has met and/or exceeded a threshold value. While various threshold values have been presented as examples, in some instances (e.g., particularly ICDs), a high sensitivity threshold value may be in a range of approximately 0.1 mV to about 0.5 mV (e.g., −0.1 mV to −0.5 mV). In some instances, a low sensitivity threshold value may be in a range of approximately 1 mV to about 2 mV (e.g., −1 mV to −2 mV). Low sensitivity thresholds and high sensitivity thresholds are optionally adjusted based on logic which may rely on intracardiac electrogram and/or other information.

Figure 5:
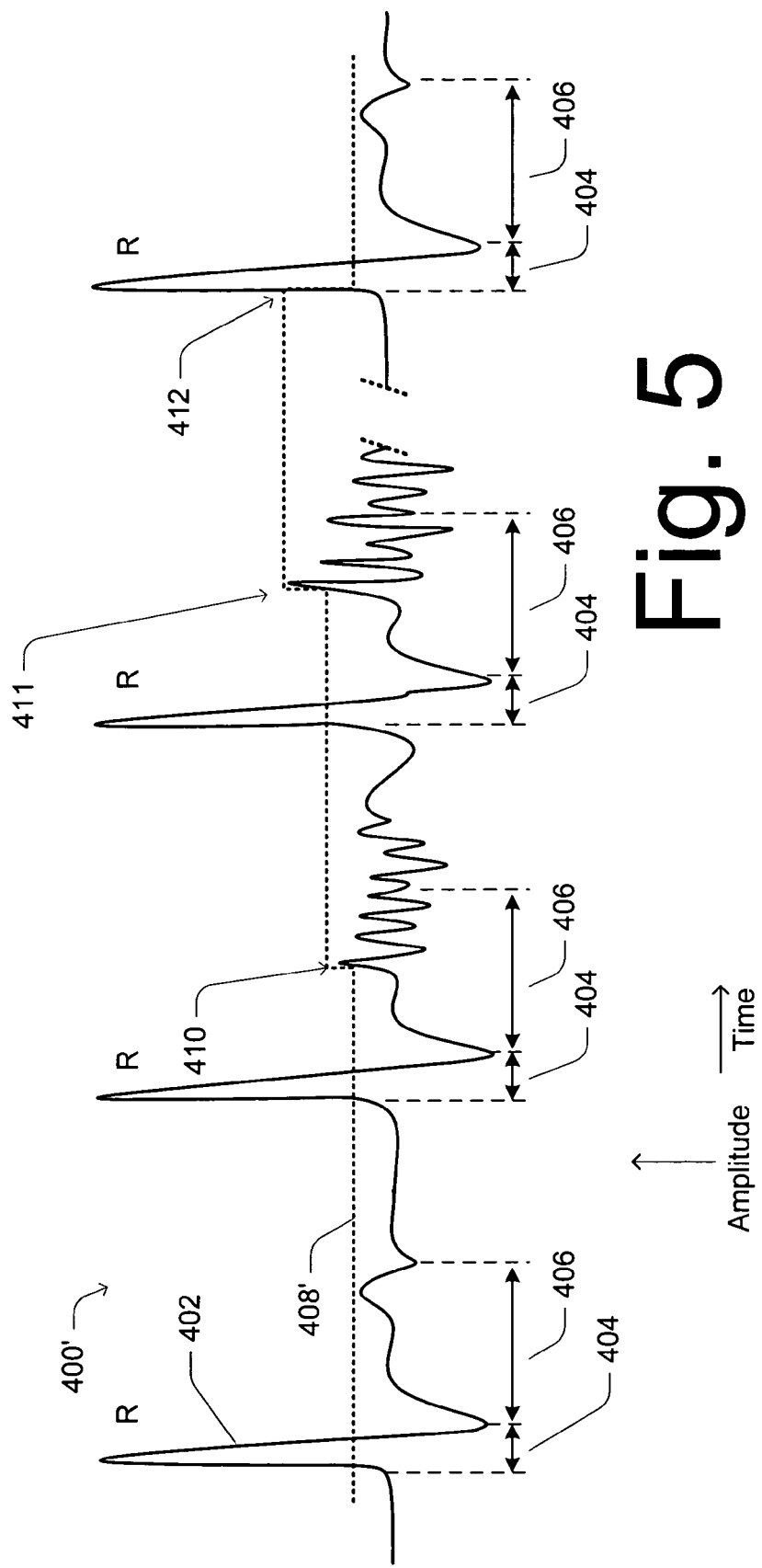

FIG. 5 depicts a timeline graph 400' that is similar to timeline graph 400, in accordance with certain further implementations of the present invention. Here, in this example, a plurality of continuingly higher level threshold values (lower sensitivity levels) is provided. Thus, at time 410, the threshold value (dashed line 408') is increased to a first higher level (i.e., an intermediate level). At time 411, however, noise is detected during a subsequent refractory period. As a result, the threshold value is further increased to a second higher level for the remainder of the defined period of time. The defined period of time may also be changed (shortened or extended) as a result of the noise detection at time 411. Although the threshold value is shown as switching at time 412 from the second higher threshold level to the lower threshold level, in certain other implementations, the switch may include switching from the second higher threshold level to the first higher threshold level during a blanking period 404, and from the first higher threshold level to the lower threshold level during a subsequent blanking period 404. This essentially provides an incremental change, either increasing to decreasing, in the sensitivity of the stimulation device, based on detected noise during one or more refractory periods.

Figure 6:
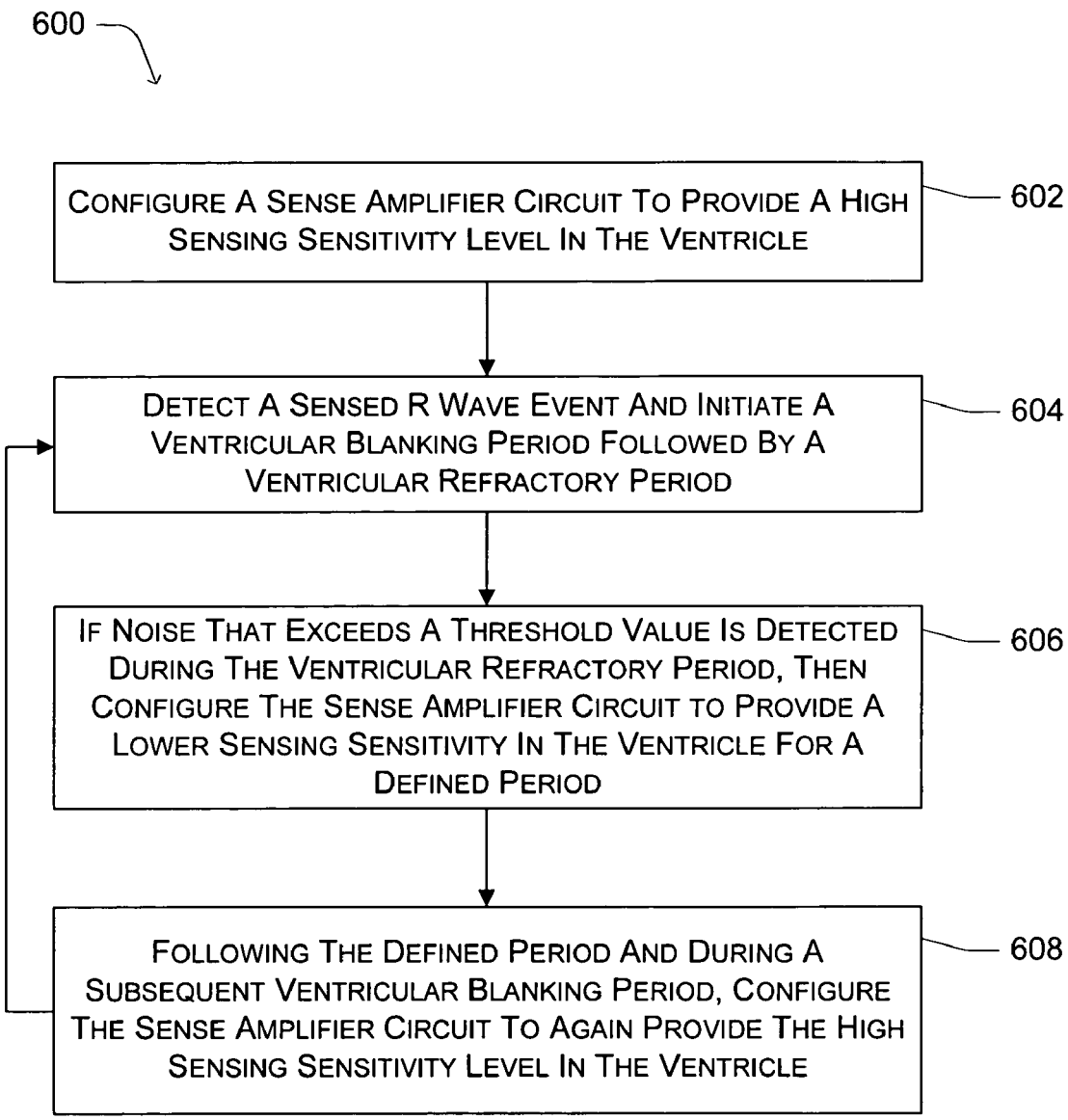
FIG. 6 is a flow diagram depicting a process for dynamically adjusting a sensitivity level to significantly avoid false positive detection of noise in an electrogram signal, in accordance with certain exemplary implementations of the present invention.

Reference is now made to the flow diagram in FIG. 6, which depicts a process 600 for dynamically adjusting sensitivity level to significantly avoid false positive detection of noise in an electrogram signal. In step 602, a sense amplifier circuit is configured to provide a high sensitivity level for sensing activity in the ventricle. In step 604, a sensed R wave or paced wave is detected, which initiates a blanking period followed by a ventricular refractory period. Next, in step 606 if noise is detected, during the ventricular refractory period, which exceeds a threshold value or level, then the sense amplifier circuit is configured to provide a lower level of sensitivity for a defined period. In Step 608, at the end of the defined period and during a blanking period associated with a subsequently detected R wave or paced wave, the sense amplifier circuit is configured to once again provide the high level of sensitivity. As shown by the arrow, process 600 may then return to step 604.

In accordance with certain other implementations of the present invention, the defined period of time can be based on the noise detection capability of one or more additional sensing and/or detecting circuits and the like that are also configured to monitor the cardiac activity. Thus, for example, the defined period of time may extend until such time that the noise level falls below a defined threshold. Thereafter, the ventricular threshold amplitude can be switched back to the lower level threshold value. This switching may, for example, occur during a blanking period to prevent artificial noise generated by the switch from interfering with the sensing of actual events, and/or noise detection during a subsequent refractory period.

As already mentioned, noise can affect sensing, detecting and therapy. For a patient with an ICD, noise-based oversensing can even cause inappropriate delivery of a defibrillation shock. Such shocks typically cause patient discomfort and apprehension. In addition, inappropriate shocks can deplete power and shorten device life and hence replacement time.

An appropriate defibrillation shock should be delivered in response to indicia of ventricular fibrillation or arrhythmia likely to progress to fibrillation (e.g., certain tachycardias, etc.). A progression to ventricular fibrillation may vary in form, scale, etc., (see, e.g., Weiss et al., "Ventricular Fibrillation: How Do We Stop the Waves From Breaking?", *Circ Res.* 2000; 87:1103-1107). A progression may include a normal sinus region, a region of early organized activation having at least some characteristics associated with or indicative of ventricular tachycardia, a transition region of more complex morphology and typically a decreased interval that may be associated with or indicative of ventricular fibrillation (VF), an early, coarse ventricular fibrillation (VF) region, a later, coarse ventricular fibrillation (VF) region (e.g., may be observed in ischemia induced arrhythmia onset), a coarse to fine ventricular fibrillation (VF) region, a fine ventricular fibrillation (VF) region and, if no intervention or termination occurs, an asystole region.

While such an exemplary progression may be indicated by cardiac waveforms of electrical behavior, a similar progression may be noted using other signals. For example, a hemodynamic sensor may detect hemodynamic behavior that indicates compromised cardiac performance. Thus, a hemodynamic sensor may indicate whether a condition is hemodynamically stable or hemodynamically unstable. Such a sensor may be used in conjunction with intracardiac electrograms. Further, intracardiac electrograms, hemodynamic signals, etc., may be analyzed using morphology or other techniques.

With respect to ventricular tachycardia (VT), waveforms may exhibit "notching" and a broad QRS-like segment (e.g., occurring over approximately 120 ms or more). Further, ST segment and T wave typically exhibit opposite polarity compared to a normal QRS. While the sinus node may be depolarizing normally, there is usually complete AV dissociation and P waves may be observed between the QRS-like segments. Ventricular rhythm during VT is somewhat regular and at a rate greater than approximately 100 bpm and generally less than approximately 220 bpm. Such information may be used in a morphology discrimination or detection module (e.g., the module 236 of FIG. 2).

Figure 7:
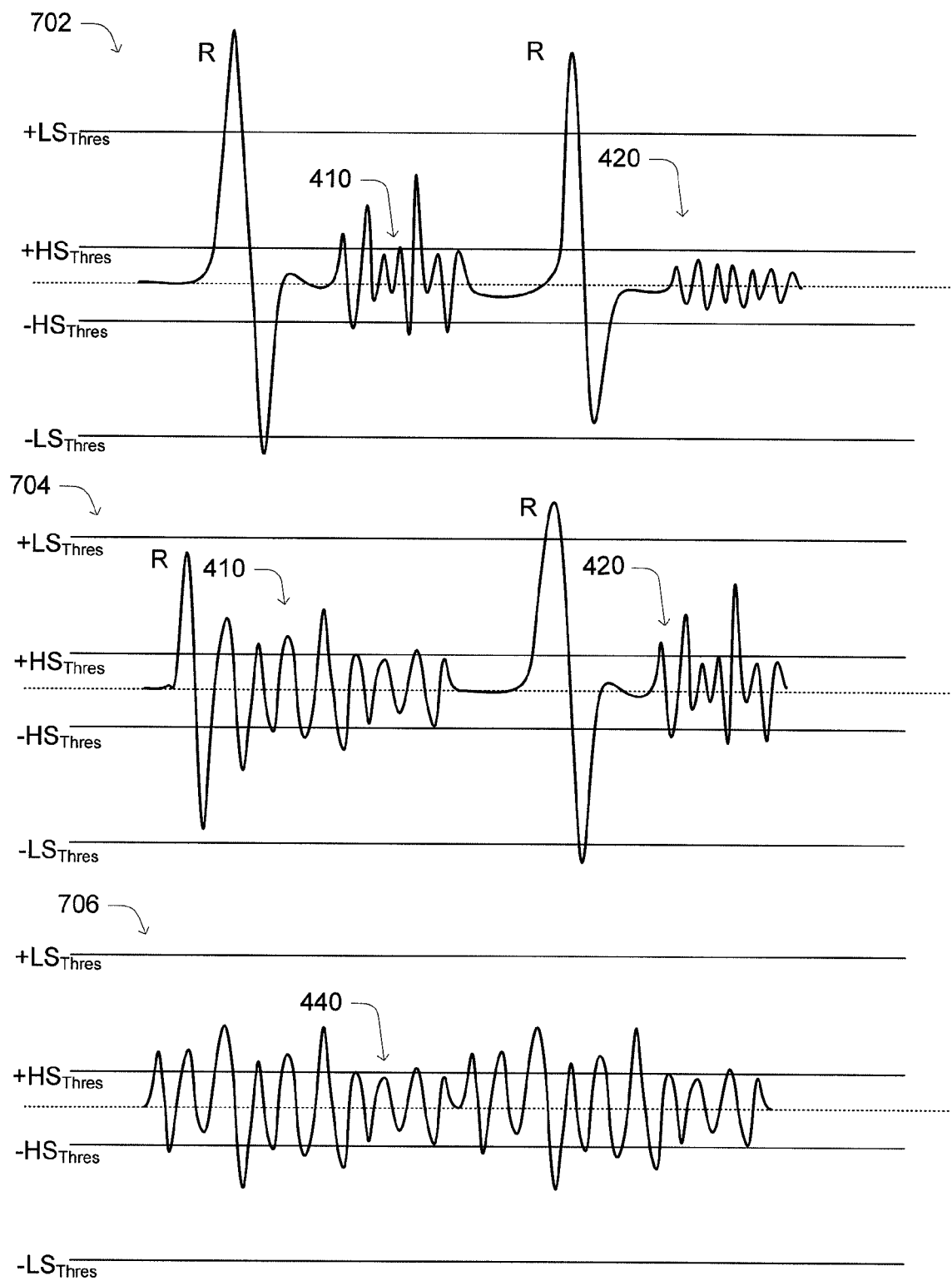
FIG. 7 is a diagram of various exemplary scenarios associated with cardiac information.

FIG. 7 shows various exemplary scenarios 702, 704, 706 that include intracardiac electrograms. Each scenario includes an upper and a lower low sensitivity threshold ($+LS_{Thres}$, $-LS_{Thres}$) and an upper and a lower high sensitivity threshold ($+HS_{Thres}$, $-HS_{Thres}$). Other scenarios may include only upper thresholds, only lower thresholds and/or a mix of one or more upper thresholds and one or more lower thresholds.

The scenario 702 includes waveforms for two cycles. The first cycle includes a wave that exceeds the upper low threshold ($+LS_{Thres}$) and that exceeds the lower low threshold ($-LS_{Thres}$). This particular portion of the first cycle waveform is considered to be associated with an R wave or QRS complex (see, e.g., label "R"). Another portion 410 follows the R wave portion. The portion 410 includes amplitudes that exceed the upper high threshold ($+HS_{Thres}$) and amplitudes that exceed the lower high threshold ($-HS_{Thres}$). The portion 410 may or may not be indicative of ventricular fibrillation. For example, the portion 410 may be noise or an actual signal associated with ventricular fibrillation.

The second cycle includes a wave that exceeds the upper low threshold (+LS$_{Thres}$). This particular portion of the first cycle waveform is considered to be associated with an R wave or QRS complex (see, e.g., label "R"). As such, a decision may be made that the portion 410 is noise and not associated with ventricular fibrillation. Further, a portion 420 follows the R wave of the second cycle wherein the portion 420 does not include any amplitudes that exceed a high sensitivity threshold (e.g., +HS$_{Thres}$, -HS$_{Thres}$). This portion may further confirm that the portion 410 should not warrant delivery of a defibrillation shock.

The scenario 704 includes waveforms for two cycles. The first cycle includes a wave that does not exceed the upper low sensitivity threshold (+LS$_{Thres}$) and that does not exceed the lower low sensitivity threshold (-LS$_{Thres}$). A portion of the waveform including this wave may be analyzed using a morphology module (e.g., the module 236 of FIG. 2). In this example, the morphology module determines that an R wave is present and hence this particular portion of the first cycle waveform is considered to be associated with an R wave or QRS complex (see, e.g., label "R"). While an R wave is shown, such a technique may be used for an evoked response following a stimulation pulse. Another portion 410 follows the R wave portion. The portion 410 includes amplitudes that exceed the upper high sensitivity threshold (+HS$_{Thres}$) and amplitudes that exceed the lower high sensitivity threshold (-HS$_{Thres}$). The portion 410 may or may not be indicative of ventricular fibrillation. For example, the portion 410 may be noise (e.g., diaphragmatic or other source) or an actual signal associated with ventricular fibrillation if for some reason fibrillation occurred after an R wave. In this example, however, an R wave follows; hence, the portion 410 following the first cycle low amplitude R wave is not indicative of ventricular fibrillation. A method may optionally use a counter to count occurrences of low amplitude R waves (e.g., as inferred by R waves of sufficient amplitude or other indicators of R waves).

The second cycle includes a wave that exceeds the upper low sensitivity threshold (+LS$_{Thres}$) and the lower low sensitivity threshold (-LS$_{Thres}$). This particular portion of the first cycle waveform is considered to be associated with an R wave or QRS complex (see, e.g., label "R"). As such, a decision may be made that the portion 410 is noise and not associated with ventricular fibrillation. A portion 420 follows the R wave of the second cycle wherein the portion 420 includes amplitudes that exceed an upper and a lower high sensitivity threshold (e.g., +HS$_{Thres}$, -HS$_{Thres}$). This portion may warrant further monitoring, especially consideration of sensor information that may be related to patient activity. Such information may help to confirm that the portion 410 is associated with noise and not a condition that would warrant delivery of a defibrillation shock.

The third scenario 706 includes a waveform 440 indicative of ventricular fibrillation, which may also include noise. The waveform 440 includes amplitudes that exceed an upper high sensitivity threshold, +HS$_{Thres}$, and amplitudes that exceed a lower high sensitivity threshold, -HS$_{Thres}$.

Figure 8:
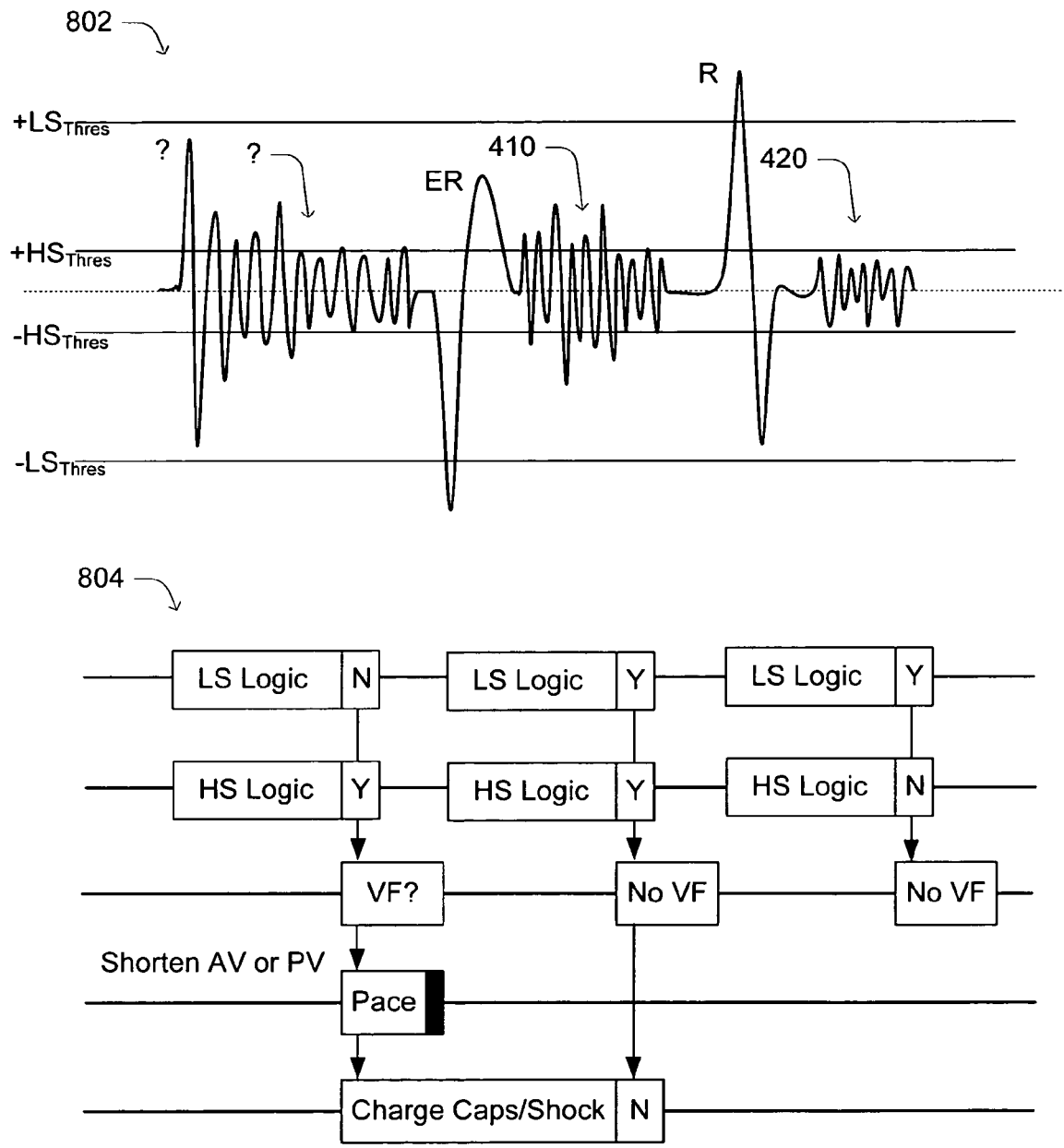
FIG. 8 is a diagram of an exemplary scenario and an exemplary method applied to the exemplary scenario.

FIG. 8 shows an exemplary scenario 802 with an associated exemplary method 804. The exemplary scenario 802 includes waveforms covering approximately three cycles. For the first cycle, logic associated with the low sensitivity threshold indicates that no amplitude exceeded the low sensitivity threshold while logic associated with the high sensitivity threshold indicates that one or more amplitudes exceeded the high sensitivity threshold. As a consequence, a determination is made that ventricular fibrillation may be present.

The determination as to ventricular fibrillation triggers various actions. For example, if ventricular pacing is not implemented, then ventricular pacing may be called for wherein an atrial-ventricular delay is optionally shortened. In addition, if a stored charge is not sufficient to deliver a defibrillation shock, then logic may call for charging of a charge storage device (e.g., one or more capacitors).

The second cycle of the exemplary scenario 802 commences with delivery of a pacing stimulus and, in this instance, an evoked response (ER). The evoked response may be detected on the basis of a morphology detector (e.g., the module 236) and/or a waveform amplitude that exceeds a low sensitivity threshold (e.g., -LS$_{Thres}$). As presented in the exemplary method 804, the low sensitivity logic indicates that a low sensitivity threshold has been exceeded. In addition, a portion 410 of the second cycle waveform that follows includes amplitudes that exceed a high sensitivity threshold. Accordingly, the high sensitivity logic indicates that a high sensitivity threshold has been exceeded. As a consequence, a determination is made that ventricular fibrillation is not present. Further, control logic associated with delivery of a defibrillation shock and/or charging of a charge storage device acts to prevent delivery of such a shock and/or to terminate charging of the charge storage device. Yet further, control logic associated with delivery of a pacing stimulus may act to terminate delivery of such a stimulus.

The third cycle of the exemplary scenario 802 commences with a waveform that exceeds a low sensitivity threshold. This condition may indicate that an R wave is present (e.g., QRS complex). Since a pacing stimulus was not delivered for the third cycle, the R wave may be classified as an intrinsic R wave (e.g., optionally based on an atrial pacing stimulus). A portion 420 of the waveform that follows the R wave does not include any amplitude that exceeds the high sensitivity threshold and the associated high sensitivity logic indicates this condition. Accordingly, logic for determinations of ventricular fibrillation indicates that ventricular fibrillation is not present. Such a determination may optionally include use of a morphology module (e.g., the module 236) and/or other physiologic information (e.g., hemodynamic information, etc.).

The various types of logic may occur sequentially or simultaneously. For example, occurrence of a "yes" LS logic state may trigger a HS logic query and also act to reset the LS logic state. In this manner, various logic actions may be avoided where deemed unnecessary. Logic flow may be determined on a patient-by-patient, risk of arrhythmia, or other basis. Where appropriate, an exemplary method may adapt logic flow based on occurrence of a number of events within a certain time period, etc.

Figure 9:
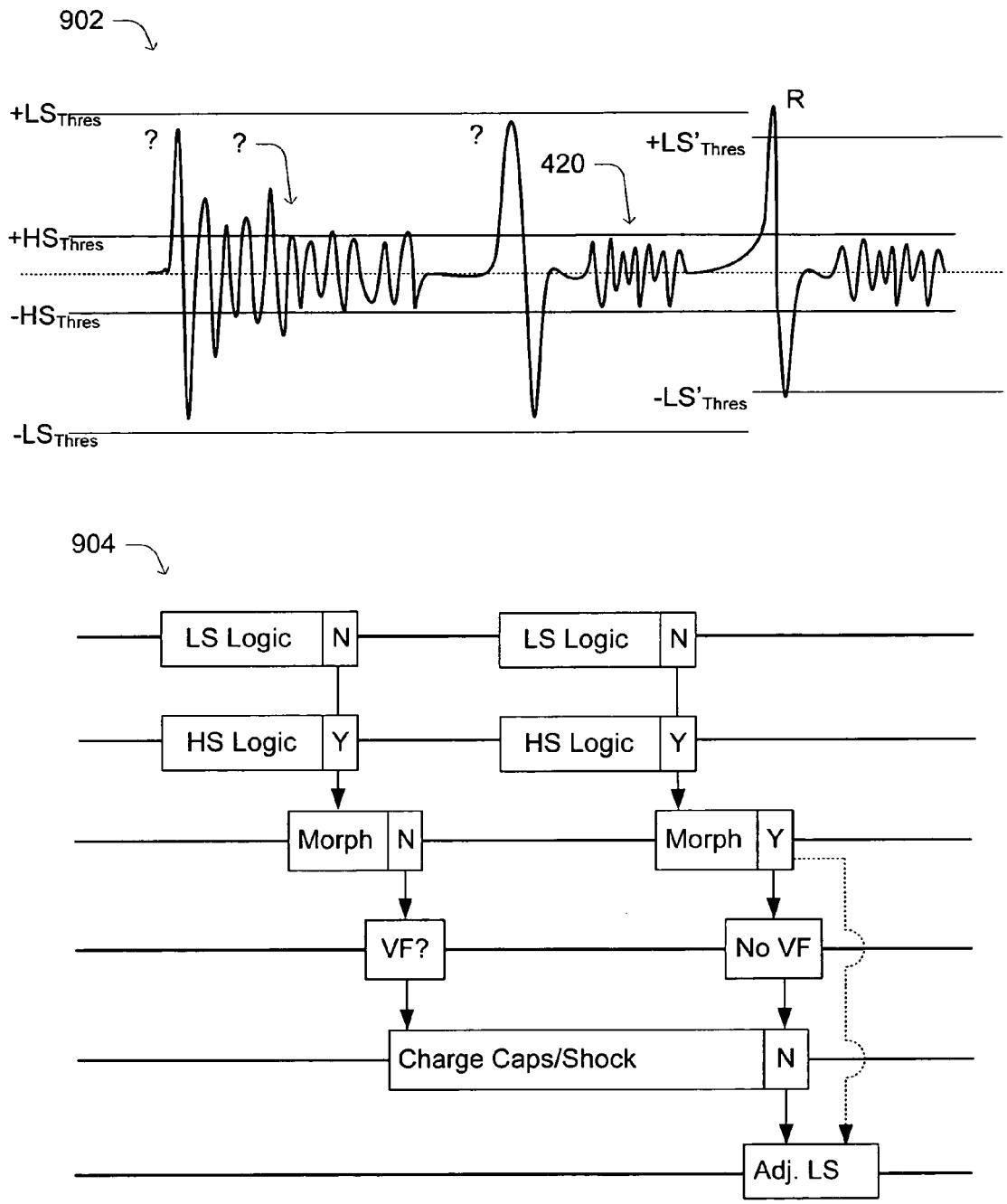
FIG. 9 is a diagram of an exemplary scenario and an exemplary method applied to the exemplary scenario.

FIG. 9 shows another exemplary scenario 902 with an associated exemplary method 904. The exemplary scenario 902 includes waveforms covering approximately three cycles. For the first cycle, logic associated with the low sensitivity threshold indicates that no amplitude exceeded the low sensitivity threshold while logic associated with the high sensitivity threshold indicates that one or more amplitudes exceeded the high sensitivity threshold. As a consequence, a morphology detection module is implemented and, in this example, the module indicates that the waveform does not exhibit characteristics of an R wave or QRS complex. In turn, a determination is made that ventricular fibrillation may be present.

The determination as to ventricular fibrillation triggers various actions. For example, if ventricular pacing is not implemented, then ventricular pacing may be called for wherein an atrial-ventricular delay is optionally shortened. In addition, if a stored charge is not sufficient to deliver a defibrillation shock, then logic may call for charging of a charge storage device (e.g., one or more capacitors).

The second cycle of the exemplary scenario 902, logic associated with the low sensitivity threshold indicates that no amplitude exceeded the low sensitivity threshold while logic associated with the high sensitivity threshold indicates that no amplitude exceeded the high sensitivity threshold. As a consequence, a morphology detection module is implemented and, in this example, the module indicates that the waveform does exhibit characteristics of an R wave or QRS complex. In turn, a determination is made that ventricular fibrillation is not present.

Subsequently, control logic associated with delivery of a defibrillation shock and/or charging of a charge storage device acts to prevent delivery of such a shock and/or to terminate charging of the charge storage device. Yet further, control logic associated with the low sensitivity threshold may action to readjust the low sensitivity threshold as the morphology detector indicated that an R wave was present yet was undetected by the low sensitivity logic because the R wave did not include any amplitude that exceeded the low sensitivity threshold. As shown in the exemplary method 904, for the exemplary scenario 902, the low sensitivity threshold is adjusted to new values $+LS'_{Thres}$ and $-LS'_{Thres}$ in response to the morphology indicating the presence of an R wave while the low sensitivity logic indicating that no amplitude exceeded the low sensitivity threshold. Other consequences may follow from such a determination and an event may be marked in an event memory. Such event memory is typically accessible telemetrically during follow-up consultation. A decrease in low threshold sensitivity may indicate a change in morphology, which may also be evidenced by morphology information. Such a decrease may indicate a worsening of cardiac condition (e.g., a progression in degree of heart failure, etc.).

An exemplary method includes sensing, in vivo, amplitude of electrical cardiac activity (e.g., using the device 100 of FIGS. 1 and 2), comparing sensed amplitude to a low sensitivity threshold (e.g., +LS or −LS of FIGS. 7, 8 and 9) where if the comparing indicates that sensed amplitude does not meet or exceed the low sensitivity threshold then further comparing the sensed amplitude to a high sensitivity threshold (e.g., +HS or −HS of FIGS. 7, 8 and 9) and if the further comparing indicates that sensed amplitude meets or exceeds the high sensitivity threshold then the method determines that ventricular fibrillation may exist.

This exemplary method may take further action, such as, sensing, in vivo, amplitude of subsequent electrical cardiac activity, comparing sensed amplitude of the subsequent electrical cardiac activity to a low sensitivity threshold where if the comparing indicates that sensed amplitude of the subsequent electrical cardiac activity meets or exceeds the low sensitivity threshold then the method determines that ventricular fibrillation does not exist.

As another example, the exemplary method may include delivering a ventricular pacing stimulus, sensing, in vivo, amplitude of electrical cardiac activity following delivery of the ventricular pacing stimulus, comparing sensed amplitude of electrical cardiac activity following delivery of the pacing stimulus to a low sensitivity threshold where if the comparing indicates that sensed amplitude of electrical cardiac activity following delivery of the ventricular pacing stimulus meets or exceeds the low sensitivity threshold then the method determines that ventricular fibrillation does not exist.

In yet another example, the exemplary method may include delivering a ventricular pacing stimulus, sensing, in vivo, amplitude of electrical cardiac activity following delivery of the pacing stimulus, comparing sensed amplitude of electrical cardiac activity following delivery of the ventricular pacing stimulus to a low sensitivity threshold where if the comparing indicates that the sensed amplitude of electrical cardiac activity following delivery of the ventricular pacing stimulus does not meet or exceed the low sensitivity threshold then the method determines that ventricular fibrillation exists.

As already mentioned, noise may interfere with sensing electrical cardiac activity. An exemplary method may include sensing, in vivo, amplitude of electrical cardiac activity, based at least in part on the sensing, detecting an R wave, comparing the sensed amplitude to a high sensitivity threshold where if the comparing indicates that sensed amplitude meets or exceeds the high sensitivity threshold then the method determines a state of patient activity. Given the comparison and a patient activity state, such an exemplary method may include classifying the sensed amplitude as including patient activity-related noise or sensing equipment-related noise. For example, where the activity state is sleep (e.g., based on heart rate, movement, etc.), then it is more likely that noise is from a source other than patient activity (excepting disruptions from apnea, etc.). On the other hand, if the patient activity state is "active", then the noise is likely to include patient activity-related noise.

As a respiratory activity can be a source of noise, an exemplary method optionally includes sensing respiration and/or determining a state of patient activity in a manner that relies at least in part on respiratory information (see, e.g., physiological sensors 270, impedance circuit 278, etc.).

An exemplary implantable device may include various features of the device 100 of FIGS. 1 and 2. For example, a device may include circuitry for sensing amplitude of electrical cardiac activity (e.g., amplifiers 244, 246 and A/D 252), logic for comparing sensed amplitude to at least a low sensitivity threshold and a high sensitivity threshold (e.g., module 238, module 236, etc.); and logic to determine whether to charge a charge storage of the implantable device based at least in part on the comparing wherein the charge storage is capable of storing charge sufficient for a defibrillation shock (e.g., module 238).

CONCLUSION

Although some preferred implementations of the various methods and arrangements of the present invention have been illustrated in the accompanying Drawings and described in the foregoing Detailed Description, it will be understood that the invention is not limited to the exemplary implementations disclosed, but is capable of numerous rearrangements, modifications and substitutions without departing from the spirit of the invention as set forth and defined by the following claims.

What is claimed is:

1. A method comprising:
   sensing, in vivo, a first waveform cycle corresponding to electrical cardiac activity, the first waveform cycle comprising a first portion and a second portion subsequent the first portion;
   comparing the amplitude of the first portion of the first cycle to a low sensitivity threshold;
   if the comparing indicates that the amplitude of the first portion of the first cycle does not meet or exceed the low sensitivity threshold then further comparing the amplitude of the second portion of the first cycle to a high sensitivity threshold;
   if the further comparing indicates that the amplitude of the second portion of the first cycle meets or exceeds the high sensitivity threshold then determining that ventricular fibrillation may exist;

if ventricular fibrillation may exist, delivering a ventricular pacing pulse;

detecting for an evoked response; and if an evoked response is detected, determining that ventricular fibrillation does not exist; terminating delivery of ventricular pacing pulses; sensing, in vivo, a subsequent waveform cycle corresponding to electrical cardiac activity, the subsequent waveform cycle comprising a first portion and a second portion subsequent the first portion; comparing the amplitude of the first portion to the low sensitivity threshold; and if the comparing indicates that the amplitude of the first portion meets or exceeds the low sensitivity threshold, confirming that ventricular fibrillation does not exist.

2. The method of claim 1 wherein the sensing occurs through use of one or more leads positioned in or proximate to a chamber of a heart.

3. The method of claim 1 wherein the comparing to a low sensitivity threshold, the comparing to a high sensitivity threshold and the determining rely on logic implemented by an implantable cardiac stimulation device.

4. The method of claim 1 wherein detecting for an evoked response comprises comparing the amplitude of sensed electrical cardiac activity at the time of the pacing pulse to the low sensitivity threshold.

5. The method of claim 1 further comprising, if ventricular fibrillation may exist, calling for the charging of a charge storage device for possible delivery of a defibrillation shock.

6. The method of claim 5 further comprising, if an evoked response is detected, terminating charging of the charge storage device.

7. The method of claim 1 wherein ventricular pacing pulses are delivered in accordance with a programmed atrio-ventricular (AV) delay and delivering a ventricular pacing pulse comprises shortening the AV delay prior to delivery of the pulse.

8. The method of claim 1 wherein confirming that ventricular fibrillation does not exist further comprises:

comparing the amplitude of the second portion to the high sensitivity threshold; and if the comparing indicates that the amplitude of the second portion does not meet or exceed the high sensitivity threshold then confirming that ventricular fibrillation does not exist.

9. An implantable medical device comprising:

means for sensing, in vivo, a first waveform cycle corresponding to electrical cardiac activity, the first waveform cycle comprising a first portion and a second portion subsequent the first portion;

means for comparing the amplitude of the first portion of the first cycle to a low sensitivity threshold;

means for further comparing the amplitude of the second portion of the first cycle to a high sensitivity threshold if the comparing to the low sensitivity threshold indicates that the amplitude of the first portion of the first cycle does not meet or exceed the low sensitivity threshold then further;

means for determining that ventricular fibrillation may exist if the further comparing indicates that the amplitude of the second portion of the first cycle meets or exceeds the high sensitivity threshold;

means for delivering a ventricular pacing pulse if ventricular fibrillation may exist;

means for detecting for an evoked response; and means for, if an evoked response is detected, determining that ventricular fibrillation does not exist; terminating delivery of ventricular pacing pulses; sensing, in vivo, a subsequent waveform cycle corresponding to electrical cardiac activity, the subsequent waveform cycle comprising a first portion and a second portion subsequent the first portion; comparing the amplitude of the first portion to the low sensitivity threshold; and if the comparing indicates that the amplitude of the first portion meets or exceeds the low sensitivity threshold, confirming that ventricular fibrillation does not exist.

* * * * *